United States Patent [19]

Zeiser

[11] Patent Number: 5,057,014

[45] Date of Patent: Oct. 15, 1991

[54] ARTICULATOR FOR DENTISTRY

[76] Inventor: Manfred P. Zeiser, Im Wolfsgalgen 8, 7141 Schwieberdingen, Fed. Rep. of Germany

[21] Appl. No.: 546,439

[22] Filed: Jun. 29, 1990

[30] Foreign Application Priority Data

Jul. 5, 1989 [DE] Fed. Rep. of Germany ....... 3922078

[51] Int. Cl.$^5$ ............................................. A61C 11/00
[52] U.S. Cl. .......................................... 433/57; 433/54
[58] Field of Search ................... 433/54, 57, 58, 60, 433/61, 65

[56] References Cited

U.S. PATENT DOCUMENTS 3,653,126  4/1972  Hansen ................................. 433/60
4,252,523  2/1981  Gayso ................................... 433/60
4,721,463  1/1988  Lee ....................................... 433/54

Primary Examiner—John J. Wilson
Assistant Examiner—Cindy A. Cherichetti
Attorney, Agent, or Firm—Michael J. Striker

[57] ABSTRACT

An articulator for dentistry comprises a base plate, an extension plate arranged at a distance from the base plate, a frame including two parallel columns and a traverse turnably supported between the columns at a distance from the base plate. The base plate and the extension plate forming mold supports. The frame has a frame opening. A pin-shaped connecting element fixes the mold supports on the frame and extends partially through the mold opening with a radial play so as to form an intermediate space between the pin-shaped connecting element and a wall of the frame opening, and a hardenable material fills the intermediate space.

22 Claims, 1 Drawing Sheet

ARTICULATOR FOR DENTISTRY

BACKGROUND OF THE INVENTION

The present invention relates to an articulator for dentistry. More particularly, it relates to an articulator which has a base plate, an extension plate, and a frame with two columns and a traverse.

Articulators of the above mentioned general type are known in the art. During performing dental works they are used for exact reproduction of anatomic chew conditions. In connection with this the teeth model is fixed in exactly reproducible way in the articulator.

Known articulators conventionally are produced with precision. However, during mounting, deviations from one device to another device cannot be completely avoided due to conventional threaded connections between the columns of the frame and the base plate or between the turnable traverse of the frame and the upper extension plate. This finally leads to differently oriented molds when the molds must be transferred from one device to another. Is is desired not to send the articulator together with the molds. The required fine adjustment is not achieved with the releasable threaded connections.

An articulator is known, in which independently on the mold position or the height of the device, a fine adjustment in all dimensions is possible. It permits transfer of molds from one device to another. Therefore the articulator communication between a technician and a dentist is dispensed with. Also articulators of different origin can be used. It is here required to screw a mounting plate in each of both mold supports. Then a model plate is arranged on a respective one of the mounting plates and connected by gypsum for equalization of space differences.

For identical connection a tensioned metal centering key is required between the mold plates. Moreover, for axes-dependent identical connection, an axiator is required for bringing the centric key in a proper position relative to the articulator axis. All these adjusting steps are performed on the one hand by dental technicians and on the other hand by dentists before the operation of the device. During performing of the method, a high degree of accuracy is achieved, however, the required parts are expensive in production and cost. Since the adjustment requires numerous working steps by a dental technician, expenses for required time must be taken into consideration. In addition, the gypsum used for bridging the space difference is susceptible to breakage and is not suitable for sending from the laboratory to the dentist and vice versa.

SUMMARY OF THE INVENTION

Accordingly, it is an object of the present invention to provide an articulator of the above mentioned general type, which avoids the disadvantages of the prior art.

More particularly, it is an object of the present invention to provide an articulator in which the model supports are fixed in a simple manner and with high accuracy on a frame.

In keeping with these objects and with others which will become apparent hereinafter, one feature of the present invention resides, briefly stated, in an articulator in which a pin-shaped connecting element fixes the mold support on the frame so that it is inserted with radial play into a frame opening to form an intermediate space between the connecting element and the wall of the opening, and a hardenable material fills the opening.

When the articulator is designed in accordance with the present invention, it achieves the above mentioned objects, and eliminates the disadvantages of the prior art.

Since in the laboratories a great number of articulators are available, it is to be understood that an articulator must be price-favorable, and there is the advantage that the mold can be exchanged with one another in articulators of the same structural series. It is also of advantage that the once produced adjustment is not changed during the daily use in the laboratories.

Theoretically, the mold supports can be fixed on the frame through a layer of hardenable material without additional connecting elements.

However, such a connection fulfills the stabilization requirements only seldom. A reinforcement between the mold support and the frame is provided when a cylindrical pin is used. The utilization of threaded bolts as a connecting element is preferable since the stability is increased due to the locking through the thread convolutions. Moreover, such a connection is releasable in the event of a defect and the parts can be used repeatedly.

The individual orientation of the mold support or mold supports is possible when the pin or the threaded bolt is fixed in an opening with a diameter insignificantly greater than the outer diameter of the connecting element. Then the mold support is individually oriented and finally in this position of the mold support, the intermediate space between the pin and the opening wall is filled with a hardenable material. The material compensates the different radial play of the connecting element relative to the opening wall, which connecting element sometimes extend non-coaxially in the opening.

It can be sufficient when only one mold support is fixed on its part of the frame with an individual orientation. In this case, an orientation of the previously fixed another mold support is required. It is better to provide such a solution when both mold supports are individually oriented relative to respective measuring points of the articulator. In the interest of a possibly high position accuracy during the hardening of the material, the position of the mold plate which forms with the mold support a non-separable unit must be guaranteed by an orienting measuring device.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF A PREFERRED EMBODIMENT

Figure 1:
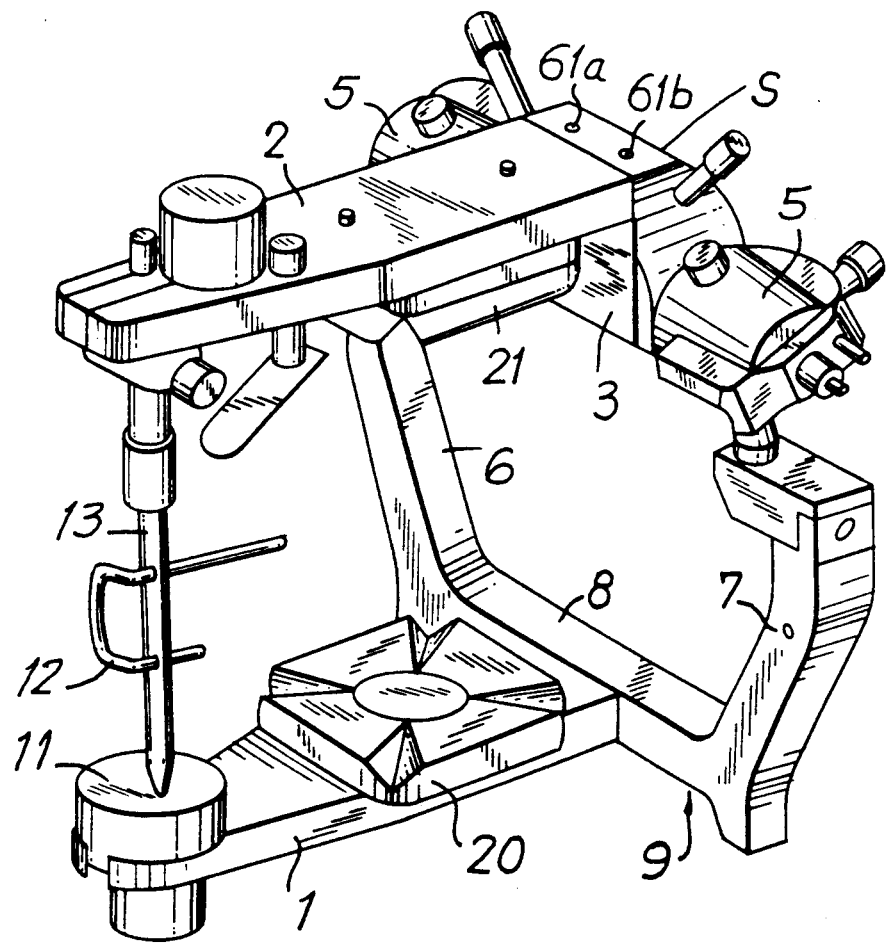
FIG. 1 is a perspective view of an articulator in accordance with the present invention.

FIG. 1 shows an articulator in a simplified and schematic manner and more particularly only those details which are important to the present invention. The articulator has a base plate which is identified with reference numeral 1 and an extension plate which is arranged at a distance from the base plate and identified with reference numeral 2. The extension plate 2 is mounted in a form-stable manner on a transverse traverse 3. The traverse 3 has an axle 4 which is turnably supported in hinge units 5 arranged on the ends of two supporting arms or columns 6 and 7. The columns 6 and 7 are formed of one piece integrally with a web 8 fixed on the base plate 1. The columns 6 and 7 with the web 8 and the hinge units 5 as well as the traverse 3 with the axle 4 can be identified as parts of a frame 9 which supports the turnable extension plate 2 on the base plate 1. The extension plate 2 in a known manner carries an incision pin 13 supported on an incision plate 11. An incision needle 12 is mounted on the incision pin 13 and its tip lies in a corner of a Bonwill triangle. The construction of such an articulator is known and does not need further explanations.

As can be seen from FIG. 1, a lower mold plate 2 is fixed on the base plate 1 and an upper mold plate 20 is fixed on the extension plate 2. Teeth molds are fixed in a proper position on the mold plates 20 and 21 in a known manner for a person skilled in the art. The base plate 1 and the extension plate 2 can be identified in the shown embodiment as mold supports.

For the present invention it is important how the mounting and orientation of the mold supports 1 and 2 is performed on the associated frame parts, namely on the traverse 3 and the web 8. The details of the mounting are shown schematically in FIG. 2 on an enlarged scale.

A mold support or the extension plate has a blind hole 30. The hole 30 opens in a wall which is located immediately near the traverse 3. The blind hole 30 is provided with a thread 32.

The traverse 3 has a throughgoing opening 40 which at one end ends in a wall portion 41 located near the extension plate 2. On the opposite end the opening 40 conically expands and identified with reference numeral 42. Such an arrangement is advantageous on mounting reasons since in this case a mounting of the both mold supports in the same mounting direction is possible.

The mold support 2 is connected with a part of a frame and particularly with the traverse 3 by a pin-shaped connecting element. This pin-shaped connecting element is formed as a threaded bolt 50. The threaded bolt 50 is a countersink head bolt and it extends partially into the blind hole 30 in the mold support 2 and partially into the opening 40 of the traverse 3. The threaded bolt 50 is screwed into the blind opening 30 with a fit. The outer thread of the threaded bolt 50 exactly corresponds to an inner thread 32 in the blind opening 30, so that the mold support 2 is fixed in a form-stable manner on the threaded bolt 50.

It is also important for the present invention to provide a possibility of the individual orientation of the mold support 2 relative to the frame part of traverse 3. For this purpose the throughgoing opening 40 in the frame part 3 has a diameter D which is greater than the outer diameter DA of the threaded screw 50. An intermediate space 60 is formed between the threaded bolt 50 and a wall 45 of the opening 40. The countersink head of the threaded bolt 50 is arranged completely in the opening 40 and an intermediate space 60 remains between the countersink head and the wall. This can be interpreted in a different way in that the threaded bolt 50 extends into the opening 40 with a radial play so that it does not contact the wall 40 of the opening at any location.

Figure 2:
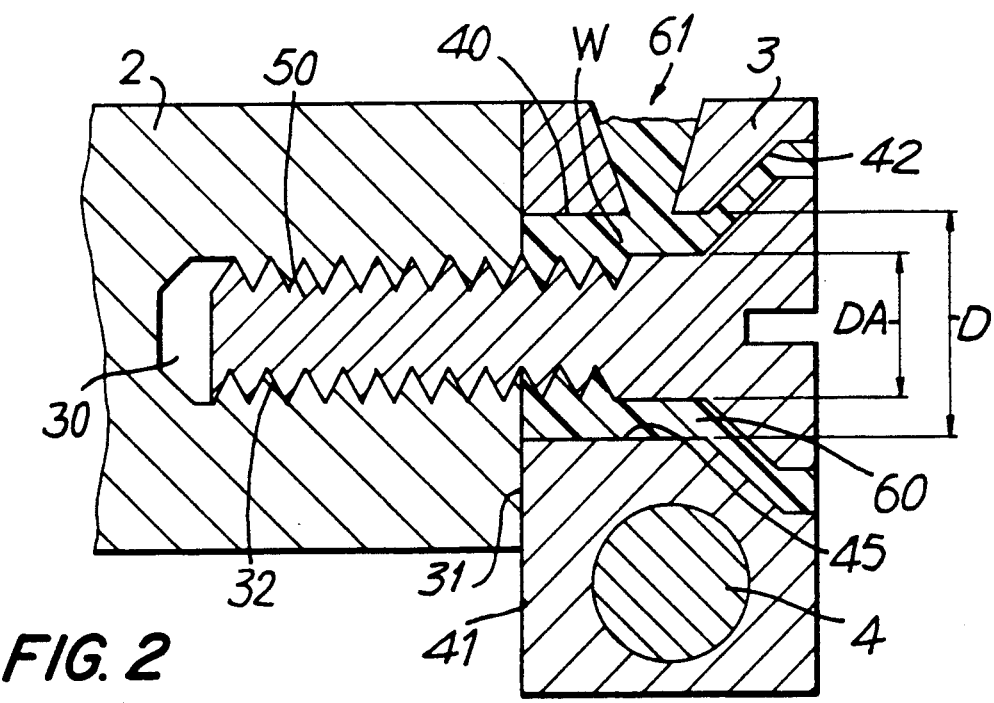
FIG. 2 is a view showing a partial section taken along the line S on the articulator of FIG. 1, on an enlarged scale.

The intermediate space 6 is filled with a hardenable material W as shown in FIG. 2. The hardenable material W is filled through a filling passage 61 which extends radially from the opening 40 and expands at the upper edge of the traverse 3 in a funnel-shaped manner. As hardenable material a finally form stable synthetic plastic material for example an epoxy or polyurethane can be used.

As can be seen from FIG. 1 the filling openings are formed as two filling passages 61a and 61b for fixing the extension plate or the upper mold support through such two connections on the traverse 3. Thereby a turning of the mold support relative to the traverse is no longer possible. Similarly, for example in accordance with the principles shown in FIG. 2, the lower mold support namely the base plate 1 is fixed on the web 8 of the frame 9.

The articulator in accordance with the present invention is produced in the following manner. The mold plates 20 and 21 are assembled with the mold supports 1 and 2 to an unseparable unit. The mold plates and the mold supports can be formed of one piece with one another. These units are then loosely fixed on the associated frame parts 3 and 8. The threaded bolt 50 is inserted through the throughgoing opening 40 into the blind hole 30. In this condition each mold support 1, 2 is oriented individually to predetermined measuring points of the articulator and/or to respective other mold supports in all recommended directions, in other words three-dimensionally. This is possible due to the play between the threaded bolt 50 and the opening 40 in the frame 3 without any difficulties. After the exact orientation, which must secure the desired position by suitable tools, measuring elements, orientation devices and the like, the hardenable material W is filled through the filling passage 61 to fill the intermediate space 60. It flows in some cases also between the neighboring walls 31 and 41 which naturally must not necessarily be oriented parallel to one another. After hardening of the material W an articulator is produced with model plates 20, 21 which are exactly oriented relative to one another and this orientation is absolutely identical for a series of molds. Thus, the articulators can be exchanged by one another.

In the preferable embodiment both mold supports 1 and 2 are fixed with individual orientation on the associated frame parts 3 and 8. In individual cases it can be sufficient when one mold support is rigidly screwed in a conventional manner, and only another mold support is fixed in accordance with the present invention in a "floating" manner.

The utilization of a threaded screw as a connecting element has the advantage in that a post-adjustment is possible. The bolt connection can be released and the hardened material can be drilled in a known manner. It is relatively simple when the opening in the frame part, as shown in the drawings, has no inner thread. On the other hand, an inner thread, due to the provided toothing with the hardenable material, increases the stability.

Due to the individual orientation of the mold supports and thereby also the mold plates and the resulting compatibility of the individual devices, a transfer of the mold from one device to the other is possible. This means that the registration can be fixed by a dentist directly in one articulator for example through an intermediate layer and a spacer bridging place on the model support in a position-accurate and reproducible manner. Therefore known auxiliary means, such as for example a transverse stand, are no longer needed. The conventional adjustment works of the articulator in laboratories are dispensed with. Transportation of the articulators between dentist and laboratory is no longer required as well.

It should also be mentioned that the articulator in accordance with the present invention can be made of conventional structural elements. Conventional extension plates and base plates can be used when the mold plates with non-uniform geometrical pattern are anchored on the opposite side of the mold supports unseparably on the mold support. For example they can be directly made on the mold supports or with interposition of spacer pieces. It is also recommended to form these nonregular geometric pattern on the mold support itself. In this case the mold support serves simultaneously as a mold plate. This nonregular geometric pattern can be formed for example by projecting conical pins extending in conical openings of conventional main plates.

Finally, it should be mentioned that the main feature of the present invention is used with advantage when a mold support is fixed as an additional part, independently of the base plate or the extension plate, directly on a frame part. Such solutions are advantageous when with conventional relatively thin main plates of synthetic plastic material, the thickness of the conventional gypsum intermediate layer can be reduced.

It will be understood that each of the elements described above, or two or more together, may also find a useful application in other types of constructions differing from the types described above.

While the invention has been illustrated and described as embodied in an articulator for dentistry, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An articulator for dentistry, comprising a base plate; an extension plate arranged at a distance from said base plate; a frame including two parallel columns and a traverse turnably supported between said columns at a distance from said base plate, said base plate and said extension plate forming mold supports, said frame having a frame opening; a pin-shaped connecting element fixing said mold supports on said frame and extending partially through said frame opening with a radial play so as to form an intermediate space between said pin-shaped connecting element and a wall of said frame opening; and a hardenable material filling said intermediate space, said mold support having a mold support opening, said connecting element being formed at a threaded screw extending partially through said mold support opening and partially through said frame opening, said mold support opening being formed as a threaded opening for said threaded bolt, said frame opening having a diameter which is greater than an outer diameter of said threaded bolt, said hardenable material filling said intermediate space between said threaded bolt and said wall of said frame opening, said frame opening being formed also as a threaded opening.

2. An articulator as defined in claim 1, wherein said mold support opening is formed as a blind threaded hole, said frame opening being formed as a throughgoing opening with a diameter greater than a diameter of said blind hole.

3. An articulator as defined in claim 2, wherein said threaded bolt is formed as a countersunk head bolt which is completely received in said frame opening, said intermediate space being formed in the region of a countersunk head of said countersunk head bolt between said bolt and the wall of said frame opening and filled with said hardenable material.

4. An articulator as defined in claim 1, wherein said frame opening is formed as a radial opening.

5. An articulator as defined in claim 1, wherein said frame opening has a funnel-shaped expanding filling passage for filling said hardenable material.

6. An articulator as defined in claim 1, wherein said extension plate is fixed individually orientably on said traverse of said frame.

7. An articulator as defined in claim 1, and further comprising two supporting columns for supporting said extension plate, said frame having a web connecting said columns with one another, said base plate being individually orientably fixed on said web.

8. An articulator as defined in claim 1, wherein said hardenable material is a finally form stable synthetic plastic material.

9. An articulator as defined in claim 8, wherein said hardenable material is an epoxy material.

10. An articulator as defined in claim 8, wherein said hardenable material is a polyurethane material.

11. An articulator as defined in claim 1, wherein at least one of said mold supports has a non-uniform geometric pattern.

12. An articulator as defined in claim 1, wherein said model support opening is formed as a blind threaded hole, said frame opening being formed as a throughgoing opening with a diameter greater than a diameter of said blind hole.

13. An articulator as defined in claim 12, wherein said threaded bolt is formed as a countersunk head bolt which is completely received in said frame opening, said intermediate space being formed in the region of a countersunk head of said countersunk head bolt between said bolt and the wall of said frame opening and filled with said hardenable material.

14. An articulator for dentistry, comprising a base plate; an extension plate arranged at a distance from said base plate; a frame including two parallel columns and a traverse turnably supported between said columns at a distance from said base plate, said base plate and said extension plate forming mold supports, said frame having a frame opening; a pin-shaped connecting element fixing said mold supports on said frame and extending partially through said frame opening with a radial play so as to form an intermediate space between said pin-shaped connecting element and a wall of said frame opening; and a hardenable material filling said intermediate space, said frame opening having a funnel-shaped expanding filling passage for filling said hardenable material.

15. An articulator as defined in claim 14, wherein said mold support has a mold support opening, said connecting element being formed as a threaded screw extending partially through said mold support opening and partially through said frame opening, said mold support opening being formed as a threaded opening for said threaded bolt, said frame opening having a diameter which is greater than an outer diameter of said threaded bolt, said hardenable material filling said intermediate space between said threaded bolt and said wall of said frame opening.

16. An articulator as defined in claim 14, wherein said frame opening is formed as a radial opening.

17. An articulator as defined in claim 14, wherein said extension plate is fixed individually orientably on said traverse of said frame.

18. An articulator as defined in claim 14, and further comprising two supporting columns for supporting said extension plate, said frame having a web connecting said columns with one another, said base plate being individually orientably fixed on said web.

19. An articulator as defined in claim 14, wherein said hardenable material is a finally form stable synthetic plastic material.

20. An articulator as defined in claim 19, wherein said hardenable material is an epoxy material.

21. An articulator as defined in claim 19, wherein said hardenable material is a polyurethane material.

22. An articulator as defined in claim 14, wherein at least one of said mold supports has a non-uniform geometric pattern.

* * * * *